United States Patent [19]

Laschewsky et al.

[11] Patent Number: 4,970,120
[45] Date of Patent: Nov. 13, 1990

[54] FILM COMPRISING UNIMOLECULAR LAYERS

[75] Inventors: André Laschewsky, Koblenz; Helmut Ringsdorf, Mainz; Werner Interthal, Rüsselsheim; Donald Lupo, Eppstein/Taunus; Werner Prass, Mainz; Ude Sheunemann, Frankfurt am Main, all of Fed. Rep. of Germany

[73] Assignee: Hoechst Aktiengesellschaft, Frankfurt am Main, Fed. Rep. of Germany

[21] Appl. No.: 219,335

[22] Filed: Jul. 14, 1988

[30] Foreign Application Priority Data

Jul. 25, 1987 [DE] Fed. Rep. of Germany ....... 3724688
Feb. 4, 1988 [DE] Fed. Rep. of Germany ....... 3803224

[51] Int. Cl.$^5$ .......................... B32B 9/04; B05D 5/06
[52] U.S. Cl. .................................. 428/411.1; 428/500; 428/412; 428/426; 428/521; 428/522; 428/457; 428/515; 428/421; 350/96.34; 427/164; 427/402; 564/306
[58] Field of Search ........................ 428/411.1, 500; 427/164, 402

[56] References Cited

U.S. PATENT DOCUMENTS 4,536,450 8/1985 Garito ........................ 428/411.1
4,598,056 7/1986 Barraud ................................ 502/4

FOREIGN PATENT DOCUMENTS 0149754 7/1985 European Pat. Off. .
0250099 12/1987 European Pat. Off. .

Primary Examiner—P. C. Sluby

[57] ABSTRACT

Film comprising at least one unimolecular layer. A film for use in nonlinear optics comprises at least one Langmuir-Blodgett layer, the layer containing or comprising a dye of the formula

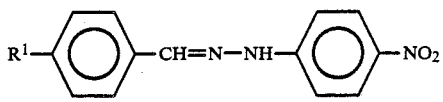

in which $R^1$ denotes a long-chain alkoxy, acyloxy, alkylamino or acylamino group. In particular when the film contains alternating layers of unsaturated amphiphilic compounds, it produces a stable multilayer having good monlinear optical properties and is suitable, for example, for electrooptical switches, diode laser frequency amplifiers or optical parametric amplifiers.

Besides the dye indicated, the unimolecular layer can additionally contain at least one second amphiphilic compound. In this case, the unimolecular layer comprises amphiphilic compounds.

4 Claims, No Drawings

FILM COMPRISING UNIMOLECULAR LAYERS

DESCRIPTION

The invention relates to a film comprising at least one unimolecular layer, which film can be used for the purpose of nonlinear optics.

Nonlinear optics (NLO) is of great importance for the future development of information technology due to its potential for rapid signal processing and transfer, and for new methods in data processing. Specific organic compounds are more effective and have faster switching times than the customary inorganic substances for nonlinear optics.

A substance has nonlinear optical properties if the polarization P produced by the interaction between the substance and a strong electrical field (a laser beam or a strong direct-current field), is dependent on higher powers of the field strength, according to equation (1):

$$P = \chi^{(1)} \cdot E_1 + \chi^{(2)} : E_1 E_2 + \chi^{(3)} \quad E_1 E_2 E_3 + \ldots \quad (1)$$

$\chi^{(1)}$, $\chi^{(2)}$ and $\chi^{(3)}$ are the so-called 1st, 2nd and 3rd order susceptibilities. E is the electrical field, which may contain components of several frequencies. Due to NLO interactions, fields of new frequencies can be generated and the refractive indices of the material can be altered. The susceptibilities $\chi^{(2)}$ and $\chi^{(3)}$ depend on the so-called molecular hyperpolarizabilities $\beta$ and $\gamma$.

Important nonlinear optical effects which are dependent on $\chi^{(2)}$ are frequency doubling of a light beam, in particular a laser beam, parametric amplification of a weak light signal and electrooptical conversion of electrical signals. In order to achieve 2nd order effects, the active molecules must be aligned non-centrosymmetrically since $\chi^{(2)}=0$ for centrosymmetric substances.

A process which can produce an ordered alignment which is particularly favorable for NLO is the Langmuir-Blodgett (LB) process. In this process, molecules are spread on a water surface, arranged parallel by reducing the area per molecule, and absorbed onto a substrate at constant shear by dipping and withdrawal of a base material. In each dipping operation, a unimolecular layer is transferred while retaining its order. In order to build up LB layers, amphiphilic molecules, i.e. molecules which have a hydrophilic end (a "head") and a hydrophobic end (a "tail") are used.

In order to produce LB layers having high 2nd order susceptibilities, organic compounds are prepared which have both high 2nd order molecular hyperpolarizabilities and amphiphilic properties. A compound has a high value for $\beta$ if it contains a conjugated electron system (for example a benzene ring) into which one or more electron-donor groups and one or more electron-acceptor groups are incorporated. A hydrophobic group is incorporated at the donor or acceptor end. The hyperpolarizability is increased if the molecule absorbs light in the wavelength range of the incident electrical field or of the field produced by the NLO (so-called resonance amplification). However, absorption is undesired in many applications since it causes losses and adversely affects the optical stability (the light intensity which can be withstood without permanent material damage). An ideal compound has a high hyperpolarizability without absorbing excessively in the desired wavelength region.

It has been found that certain amphiphilic dyes have these properties.

The invention thus relates to the film described in the claims.

The film according to the invention comprises at least one unimolecular layer which contains or comprises an amphiphilic compound of the formula (I)

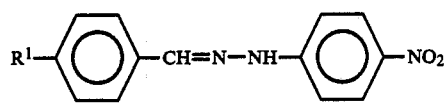

in which $R^1$ denotes the $CH_3-(CH_2)_m-O-$,

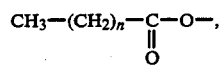

$CH_3(CH_2)_nN(CH_2)_lH$ or $CH_3(CH_2)_n(CO)N(CH_2)_lH$ radical and m is a number from 10 to 25, preferably 15 to 19, n is a number from 8 to 22, preferably 10–14, and l is a number from 0–25, preferably 0–4 or 14–22.

In the layer, the molecules of the compound of the formula (I) are oriented in the same direction, parallel to one another and non-centrosymmetrically. In many cases, they are essentially perpendicular to the layer plane, which is advantageous.

In order to build up relatively thick films while retaining the non-centrosymmetry, the film according to the invention comprises at least two unimolecular layers of different composition. In most cases, adjacent layers each have different composition. However, the different composition is not a basic prerequisite. For example, a layer which contains or comprises a compound of the formula (I) alternates with a layer which does not contain or comprise a dye of the formula I but contains or comprises another amphiphilic compound, in particular without a chromophore. The layers which comprise a compound of the formula (I) may also contain small amounts of salts or the sub-phase used during spreading.

If $A^1$, $A^2$ and $A^3$ denote different amphiphiles without a chromophore and if $F^1$, $F^2$ and $F^3$ denote different dyes of the formula I, various ways of building up the layer can be illustrated schematically as follows:

$F^1/F^2/F^1/F^3$
$A^1/F^1/A^1/F^1$
$A^1/F^1/A^2/A^2$
$F^1/A^1/A^2/A^3$
$F^1/F^1/F^1/F^1$
$F^1/F^2/F^1/F^2$
$F^1/F^2/A^1/A^2$
$F^1+A^1/F^2/F^1/F^3$
$A^1/F^1+A^1/A^1/F^2+A^2$
$A^1+F^1/A^1/A^2/A^3$
$A^1+F^1/A^2+F^2/A^1+F^1/A^2+F^2$

Amphiphilic compounds simultaneously contain at least one hydrophilic and at least one hydrophobic group in the molecule.

The hydrophobic part of the second amphiphilic compound should have a certain minimum length. It is preferred for the second amphiphilic compound to contain at least one hydrophobic part containing at least 8 carbon atoms and at least one of the following polar groups: ether, hydroxyl, carboxylic acid, carboxylate, amine, carboxamide, ammonium salt, sulfate, sulfonic acid, phosphoric acid, phosphonic acid, phosphonate, phosphonamide, phosphoric acid ester or phosphoramide group.

It is preferred for the amphiphilic compound to comprise at least one hydrophobic part having at least 8 carbon atoms and at least one polar part which is selected from the following groups

—$OR^5$

—$COOR^3$

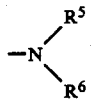

—N    B

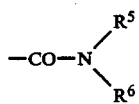

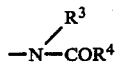

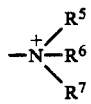

—$SO_3H$

—$OSO_3R^3$

—$OPO(OR^3)(OR^4)$

—E

—O—E

—$NR^3$—E, where $R^3$ to $R^7$, B and E have the following meanings:
$R^3$ and $R^4$, independently of one another, denote H or $C_1$–$C_3$-alkyl,
$R^5$, $R^6$ and $R^7$, independently of one another, denote H, $C_1$–$C_4$-alkyl, —$C_2H_4OH$ or —$CH_2$—CHOH—$CH_3$, in particular H or $CH_3$ denotes a divalent organic radical, so that —N⌒B forms a nitrogen-containing heterocyclic ring, in particular a 5- or 6-membered, saturated or unsaturated heterocyclic ring containing 1 to 3 carbon atoms or nitrogen and oxygen atoms or nitrogen and sulfur atoms, and

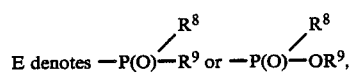

where $R^8$ and $R^9$, independently of one another, represent 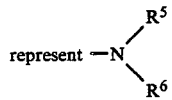

For example, the amphiphilic compound may be a fatty acid of the general formula II $$CH_3(CH_2)_mCO_2H \qquad (II)$$

where m denotes a number from 8 to 25, preferably 12 to 22.

The amphiphilic compound employed is advantageously an unsaturated acid amide of the general formula III

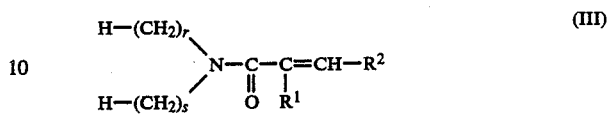

in which
$R^1$ denotes H, Cl, F, CN or $(CH_2)_tH$,
$R^2$ denotes H, $(CH_2)_uH$ or —CH=CH—$(CH_2)_uH$,
r and s, independently of one another, denote a number from 0–22 and
t and u, independently of one another, denote a number from 0–24, in particular 0–18.

r is preferably a number from zero to 18 and s is preferably zero.

Production of films and unimolecular layers by means of the LB technique usually takes place on water surfaces. It is therefore preferred for the amphiphilic compound to have only low water solubility, in particular a water solubility of less than 5 g/l at 20° C.

In order to achieve sufficiently low water solubility of this amphiphilic compound, it is preferred that at least one of the values for r, s, t and u is at least 10. However, it is not necessary that all the values are at least 10. A particularly preferred possibility is that one of the values for t and u is at least 10 and the other value is a maximum of 1. Another particularly preferred possibility is that the value for r is at least 10 and the values for t and u are a maximum of 1.

It is also possible to employ as amphiphilic compound saturated acid amides of the general formula IV

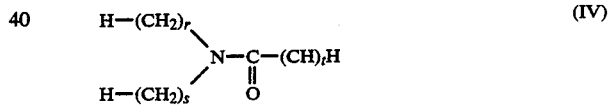

where r and s, independently of one another, denote a number from 0–22 and t denotes a number from 0–24, and at least one of the values for r, s and t is at least 8.

Here too, it is appropriate, in order to achieve adequate hydrophobicity, that at least one of the values for r, s and t is at least 10. A particularly preferred possibility is that the values for r and s are a maximum of 1 and the value for t is at least 10. Another particularly preferred possibility is that the value for r is at least 10 and the value for t is a maximum of 1.

It is favorable if the chain lengths of the amphiphilic dyes and of the second amphiphilic compound employed are matched to one another. It is therefore preferred that the length of the alkyl chain of the amphiphilic phenylhydrazone (dye) and of the hydrophobic part of the second amphiphilic compound employed differ by a maximum of 1 nm. If the second amphiphilic compound should contain two or more hydrophobic parts, the longest hydrophobic part is the decisive factor.

In order to produce the films according to the invention, the compounds of the formula I and/or the chromophore-free amphiphilic compounds are applied (spread) in a high-volatility solvent onto the surface of the sub-phase in a Langmuir-Blodgett film balance. The solvent evaporates and the compounds remain on the surface. The mean area per molecule is calculated from the dimensions of the surface, the spread volume and the concentration of the solution.

The spread molecules are pushed together using a barrier, the chains being oriented essentially perpendicular to the boundary layer as the density increases. Phase transitions during compression of the molecules can be detected in the shear area isotherms. Phase states can be detected in the shear area isotherms. During compression, self-organization of the molecules in the boundary layer causes production of a highly ordered, unimolecular film whose constant layer thickness is determined by the chain lengths of molecules. Typical thickness of a film of this type is between 2 and 3 nm, which corresponds approximately to the length of the longest molecules in the layer.

Depending on the hydrophilicity of the substrate (=base material), the hydrophilic or hydrophobic ends of the amphiphilic molecules applied (including the dye) face the substrate.

The unimolecular layer initially formed on the water surface is removed from the water surface with retention of the molecular order by immersion and removal of a clean suitable base material. By repeating this process, several unimolecular layers can be applied successively, and the thickness of the film obtained can thus be varied.

Suitable base materials are solids having clean surfaces, such as, for example, glass, ceramic or metal sheets, plastic sheets made of, for example, PMMA, polystyrene, polycarbonate, polyethylene, polypropylene or polytetrafluoroethylene, or metallic coatings on the substrates mentioned. Furthermore, metal foils can be used as base materials. In this case, however, the nonlinear optical properties can only be observed in reflected light.

In order to experimentally determine the value for the 2nd order susceptibility ($\chi^{(2)}$), the phenomenon of frequency doubling, in which incident light of frequency $\omega$ is converted in an active substance into light of frequency $2\omega$.

The film according to the invention, in particular if it contains alternating layers of compounds of the formula (I) and other amphiphilic compounds, produces a stable multilayer having good nonlinear optical properties. It is therefore suitable, for example, for electrooptical switches, diode laser frequency doublers or optical parametric amplifiers, for example as so-called boosters for weak light signals in optical signal communication networks.

For specific applications, for example the construction of planar nonlinear optical fibers using light of certain polarization, it is advantageous for the chromophores of the dye (so-called active groups) to be oriented essentially perpendicular to the surface of the substrate (of the base material of the layer). In the case of some dyes, however, it is apparent that the chromophores are oriented essentially parallel to the surface, although the long hydrophobic alkyl chains are oriented essentially perpendicular.

This also applies to the above-described dyes of the formula (I) containing an acyloxyphenyl group.

It has been found that an essentially perpendicular orientation of the chromophores in these dyes can be achieved by depositing the dyes in mixtures with other amphiphilic substances in unimolecular oriented layers.

In this case, it is necessary, with respect to the concentration of the other amphiphilic compounds, that certain concentrations are observed. If their amount is less than 10 mol-%, only a weak orientation effect is observed, or none at all.

A preferred embodiment of the invention therefore concerns a film comprising at least one unimolecular layer which contains, besides the amphiphilic phenylhydrazone of the general formula (Ia)

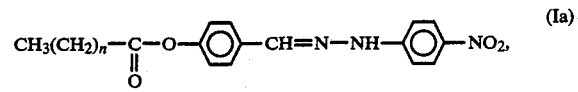

(Ia)

at least one further amphiphilic compound in a proportion from 10 to 90 mol-%. The sum of all amphiphilic compounds here is 100%. In this case, phenylhydrazones in whose general formula n has a value from 10–14 are preferably used.

The intended effect occurs particularly clearly when the proportion of the second amphiphilic compound is 40–75 mol-%.

Even the film according to the invention applied to the base material, whose layers contain dyes of the formula Ia containing acyloxy groups and amphiphilic compounds, is stable and has good nonlinear optical properties. The molecules are arranged parallel and in the same direction, i.e. non-centrosymmetrically. By adding this amphiphilic compound, films can be obtained in which not only the hydrophilic part, but also the chromophore, of the dye molecules is oriented perpendicular to the layer plane.

The dyes of the general formula I can be obtained as follows:

(1) Ethers Alkyl bromide+p-hydroxybenzaldehyde→p-alkoxybenzaldehyde p-alkoxybenzaldehyde+p-nitrophenylhydrazine→the corresponding nitrophenylhydrazone.

(2) Esters Acyl chloride+p-hydroxybenzaldehyde→p-acyloxybenzaldehyde. p-Acyloxybenzaldehyde+p-nitrophenylhydrazine→the corresponding nitrophenylhydrazone.

(3) Monoalkylamines Carboxylic acid+aniline→acylaniline. Acylaniline+lithium aluminum hydride→monoalkylaniline. Monoalkylalanine+dimethylformamide/phosphorus oxychloride→p-monoalkylaminobenzaldehyde (Vilsmeier) p-Monoalkylaminobenzaldehyde+p-nitrophenylhydrazine→the corresponding nitrophenylhydrazone.

(4) Dialkylamines Excess of alkyl bromide+aniline→N,N-dialkylaniline. Introduction of an aldehyde group using dimethylformamide (=DMF)/phosphorus oxychloride→p-dialkylaminobenzaldehyde. p-Dialkylaminobenzaldehyde+p-nitrophenylhydrazine→the corresponding nitrophenylhydrazone.

(5) Amide p-Monoalkylaminobenzaldehyde (cf. 3.) +acyl chloride→p-(N-acyl-N-alkylamino)benzaldehyde. From this, the corresponding nitrophenylhydrazone by means of p-nitrophenylhydrazine.

(6) Dialkylamine containing different alkyl groups Alkylaniline+acyl chloride→N-alkyl-N-acylaniline. Reduction using lithium aluminum hydride→p-(N-alkyl$^1$-N-alkyl$^2$-amino)benzaldehyde.

From this, the corresponding nitrophenylhydrazone by means of p-nitrophenylhydrazine.

The following Examples illustrate the invention.

EXAMPLE 1

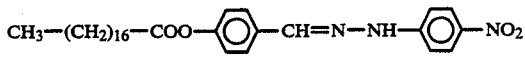

6.11 g of 4-hydroxybenzaldehyde were dissolved in 200 cm$^3$ of dry methylene chloride, 8 cm$^3$ of triethylamine were added, and the solution was cooled to 5° C. in an ice bath. 15.1 g of stearyl chloride, dissolved in 100 cm$^3$ of dry methylene chloride, were added dropwise at this temperature over the course of 20 minutes. The reaction solution was subsequently washed with 1M HCl, water, 5% strength Na$_2$CO$_3$ solution and again with water, the organic phase was dried using sodium sulfate, and the solvent was stripped off in vacuo. For purification, the product was recrystallized twice from methanol. Melting range: 59.5°–60.5° C. Yield: 12.74 g 3.89 g of the stearate were added to a solution of 1.53 g of 4-nitrophenylhydrazine in a mixture of 10 cm$^3$ of glacial acetic acid, 10 cm$^3$ of water and 100 cm$^3$ of ethanol. The mixture was stirred at room temperature for two hours, and the orange precipitate was filtered off under suction and recrystallized several times from methanol, ethyl acetate and acetone. Melting range: 131°–134° C. Yield: 1.28 g

EXAMPLE 2

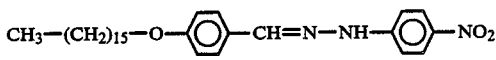

11.6 g of potassium carbonate were ignited for 2 hours at 800° C. and, after cooling, suspended in a solution of 9.77 g of 4-hydroxybenzaldehyde, 24.43 g of 1-bromohexadecane and 100 mg of potassium iodide in 600 cm$^3$ of dry acetone. The suspension was refluxed for 60 hours with exclusion of moisture and subsequently filtered whilst hot. 600 cm$^3$ of hexane were added to the filtrate, and the solution was washed with 10% strength Na$_2$CO$_3$ solution and water. The organic phase was dried using sodium sulfate, and the solvent was stripped off in vacuo. The product was subsequently recrystallized again from methanol. Melting range: 51°–59° C. Yield: 14.7 g 3.47 g of the hexadecyl ether were added to a solution of 1.53 g of 4-nitrophenylhydrazine in a mixture of 10 cm$^3$ of glacial acetic acid, 10 cm$^3$ of water and 100 cm$^3$ of ethanol, and the mixture was stirred at room temperature for 2 hours. The orange precipitate was filtered off under suction and recrystallized several times from ethyl acetate. Melting range: 115°–117° C. Yield: 3.16 g

EXAMPLE 3

A silicon plate (4 cm × 1 cm) was cut out of a silicon wafer and cleaned as follows:

(1) Treatment for 1 hour in an ultrasound bath in a mixture comprising one part of 30% strength H$_2$O$_2$ and four parts of concentrated sulfuric acid. Subsequently rinse with clean water.

(2) Dip for 20 seconds into an ammonium fluoride-buffered HF solution and subsequently rinse with clean water.

After this treatment, the silicon plates were hydrophobic (contact angle with water: 75° C.).

Layers of N-octadecylacrylamide were transferred onto the silicon plate by the method of Langmuir and Blodgett by spreading 0.1 cm$^3$ of a 10$^{-4}$ molar solution of N-octadecylacrylamide in n-hexane on an aqueous sub-phase on the tank of a Langmuir film balance. By reducing the size of the monofilm-covered water surface, the shear was adjusted to 25 mN/m and kept constant at this value (area requirement at this shear: 0.21 nm$^2$/molecule). The silicon plate was then dipped vertically from above through the water surface into the tank of the film balance (dipping speed: 20 mm/min) and removed again after a short pause (10 seconds) at the lower reversal point (removal speed: 10 mm/min). Both during the dipping and removal operation, a monolayer was transferred onto the silicon plate. By repeating the dipping operation and by varying the dipping depth, 10, 20, 30, 40 and 50 layers were transferred in this way onto a base material. By means of ellipsometer measurements, the thicknesses and refractive index of the LB films were subsequently measured. (Result: layer thickness: 2.41 nm per monolayer; refractive index 633 nm: 1.51)

EXAMPLE 4

23.28 g (0.25 mol) of freshly distilled aniline and 167.94 g (0.55 mol) of 1-bromohexadecane were combined and stirred for 3 days at 90° C. under a nitrogen atmosphere. 700 ml of toluene were then added, and the mixture was washed by shaking with 10% strength Na$_2$CO$_3$ solution. The mixture was subsequently acidified using 5% strength HCl, and the precipitated hydrochloride was filtered off. A further 700 ml of toluene were then added, the mixture was washed by shaking with 10% Na$_2$CO$_3$, the organic phase was dried using Na$_2$SO$_4$, and the solvent was removed under reduced pressure. After recrystallizing twice from ethanol, 56.5 g (42% of theory) of colorless crystals were obtained which melt at 48°–49° C. A slurry of 10 g (18.5 mol) of N,N-dihexadecylaniline in 20 g of freshly distilled DMF was cooled to 5° C., and 2.8 g (18.5 mmol) of POCl$_3$ were added over the course of 5 minutes. When the addition was complete, the mixture was stirred at 20° C. for one hour and at 80° C. for 3 hours. After cooling, the reaction mixture was decomposed using 40 g of ice water and neutralized using 10 ml of 5M NaOH solution. The precipitate produced was filtered off under suction and recrystallized from methanol and hexane. 5.1 g (48% of theory) of colorless crystals of melting point 56°–57° C. were obtained.

0.1 g (0.18 mmol) of N,N-dihexadecylaminobenzaldehyde and 0.4 g (2.6 mmol) of 4-nitrophenylhydrazine were dissolved by warming briefly in a mixture of 5 ml of glacial acetic acid, 3 ml of water and 30 ml of ethanol. After the mixture had been left to stand overnight, the dark red crystals produced were filtered off and recrystallized from hexane and methanol. 50 mg (39% of theory) of red crystals of melting point 47° C. were obtained.

| Elemental analysis: | C | H | N |
|---|---|---|---|
| calculated: | 76.65% | 10.86% | 7.95% |
| found: | 76.14% | 10.78% | 7.80% |

EXAMPLE 5

A silicon plate was cleaned as in Example 3 and coated, analogously to Example 3, with 10, 20, 40 and 60 monolayers of the dye from Example 2 by the Langmuir-Blodgett process (sub-phase: water; temperature: 20° C.; shear: 35 mN/m; area requirement: 0.26 nm²/molecule; dipping speed: 20 mm/min; removal speed: 10 mm/min). The layers were investigated ellipsometrically as in Example 3. The layer thickness determined therefrom was 2.75 nm per monolayer and the refractive index at 633 nm was 1.58.

EXAMPLE 6

As in Example 5, 10, 20, 40 and 60 monolayers of the dye synthesized according to Example 1 were transferred onto a silicon plate and the ellipsometric layer thickness and refractive index at 633 nm were determined. The layer thickness per monolayer was 2.75 nm and the refractive index was 1.58.

EXAMPLE 7

A glass specimen slide (76 mm×26 mm) was cleaned by the following method:

The glass was subjected to ultrasound for one hour in a mixture comprising one part of 30% strength hydrogen peroxide and four parts of concentrated sulfuric acid. The specimen slide was then rinsed with water and treated with ultrasound for 15 minutes at 50° C. in a cleansing solution (2-4 g/l). The slide was subsequently again rinsed thoroughly with clean water.

The specimen slide thus treated was dipped into the aqueous sub-phase in a Langmuir film balance, the dye synthesized in Example 1 was spread on the water surface and compressed, and the glass slide was removed from the sub-phase (sub-phase: water; temperature: 20° C.; shear: 35 mN/m; area requirement: 0.24 nm²/molecule; removal speed: 10 mm/min). During this operation, a monolayer was transferred onto both the front and back of the glass plate.

The coated glass plate was clamped into the sample chamber of an apparatus for determining the nonlinear optical susceptibility and was measured. The 2nd order susceptibility was $0.56 \times 10^{-6}$ esu and the nonlinear polarization was $108 \times 10^{-30}$ esu.

The apparatus for determining the nonlinear optical susceptibility works as follows:

An Nd:YAG laser generates a pulsed laser beam of wavelength 1,064 nanometer ($\omega=9{,}398$ cm$^{-1}$), which is split into 2 sub-beams by a semi-transparent mirror. The first sub-beam is converted, by frequency doubling in a reference sample, into a reference beam of wavelength 532 nanometers ($2\omega=18{,}796$ cm$^{-1}$), which is measured by a photo-multiplier. The second sub-beam hits a glass slide, on both sides of which the Langmuir-Blodgett layer to be investigated has been applied. The direction of the laser beam forms an angle $\theta$ with the perpendiculars to the glass slide plane. After irradiation of the Langmuir-Blodgett layer, the light beam likewise contains light of frequency $2\omega$. The basic wave ($\omega$) remaining is then absorbed by filters. The intensity of the (frequency-doubled) beam remaining is measured by a second photo-multiplier. The intensity is divided by the intensity of the reference signal in order to be able to compensate for variations in the laser power in the calculations. The dependency of the standardized signal on the angle of rotation $\theta$ is observed or calculated. The second order susceptibility and the orientation of the chromophores on the surface can be determined from the amplitude and angle dependency of the frequency-doubled signal. The thickness and refractive index of the LB layer, which are likewise involved in the calculation, can be determined by ellipsometry.

EXAMPLE 8

A glass specimen slide was coated as in Example 7 with a monolayer of the dye synthesized in accordance with Example 2, and the susceptibility and the nonlinear polarization were measured. The 2nd order susceptibility was $1.7 \times 10^{-6}$ esu and the nonlinear polarization was $325 \times 10^{-30}$ esu.

EXAMPLE 9

A glass specimen slide was cleaned as in Example 7 and coated with a monolayer of N-octadecylacrylamide (subphase: water; temperature: 20° C.; shear: 25 mN/m; removal speed: 10 mm/min). The film was then absorbed from the water surface of the film balance, the dye synthesized in accordance with Example 2 was spread, and a dye monolayer was transferred by dipping in the base material (shear: 35 mN/m; dipping speed: 20 mm/min). The dye film was subsequently absorbed from the water surface, N-octadecylacrylamide was spread, and a mono-layer was again transferred on removal after dipping.

This procedure was continued until an alternating film comprising 3 layers of acrylamide and 2 layers of dye had been built up. The 2nd order susceptibility was measured on this film as in Example 7. Its value was $0.27 \times 10^{-6}$ esu.

EXAMPLE 10

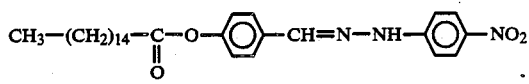

6.11 g of 4-hydroxybenzaldehyde were dissolved in 200 ml of dry methylene chloride, 8 ml of triethylamine were added, and the solution was cooled to 5° C. in an ice bath. 13.7 g of palmityl chloride, dissolved in 100 m of dry methylene chloride, were added dropwise at this temperature over the course of 30 minutes. The reaction solution was subsequently washed with 1M hydrochloric acid, water, 5% strength Na$_2$CO$_3$ solution and again with water, the organic phase was dried using sodium sulfate, and the solvent was stripped off in vacuo. For purification, the p-palmitoyloxybenzaldehyde was recrystallized from methanol. Melting range: 68°-71° C. Yield: 14.02 g 3.16 g of the palmitate were added to a solution of 1.53 g of 4-nitrophenylhydrazine in a mixture of 10 ml of glacial acetic acid, 10 ml of water and 100 ml of ethanol. The mixture was stirred at room temperature for two hours, and the orange precipitate was filtered off under suction and recrystallized twice from methylene chloride and once from methanol. Melting range: 129°-132° C. Yield: 2.51 g

EXAMPLE 11

Six glass specimen slides (76 mm×26 mm) were cleaned by the following method: The glass was treated with ultrasound for one hour in a mixture comprising one part of 30% strength hydrogen peroxide and four parts by volume of concentrated sulfuric acid. The specimen slide was subsequently rinsed with water and treated with ultrasound for 15 minutes at 50° C. in a solution of alkaline cleanser (4 g/l of Extran(R) liquid from Merck AG). The slide was subsequently rinsed thoroughly with clean water.

Mixtures of the dye synthesized in Example 10 and N-octadecylacrylamide in the molar ratios 95:5, 90:10, 80:20, 60:40 and 40:60 were prepared.

For each mixture, a cleaned object slide was dipped into the aqueous sub-phase in a Langmuir film balance, the dye/N-octadecylacrylamide mixture was spread on the surface and compressed, and the base material was removed from the sub-phase. During this procedure, a monolayer was transferred onto both the front and back of the glass plate. (Absorption conditions: sub-phase water, temperature 20° C., shear 30 mN/m, removal speed 1.5 cm/min).

The coated glass plates were clamped into the sample chamber of an apparatus for determining the nonlinear optical susceptibility and measured as described in Example 7. From the measurement results, it was possible to determine that the chromophores in the layers of the mixtures having the ratios 95:5, 90:10 and 80:20 (dye/N-octadecylacrylamide) were essentially parallel to the surface. However, the chromophore is oriented essentially perpendicular to the surface in layers of mixtures containing an N-octadecylacrylamide proportion of 40 mol-% or more.

EXAMPLE 12

Five glass specimen slides were cleaned as in Example 11. Mixtures of the dye synthesized in Example 10 and palmitic acid were prepared in the molar ratios 95:5, 90:10, 80:20, 60:40 and 40:60.

For each mixture, a monolayer was absorbed onto a base material as in Example 11 (same absorption conditions). The coated glass plates were clamped into the specimen chamber of the apparatus for determining the nonlinear optical susceptibility and measured. From the measurement results, it was possible to determine that the chromophores were essentially parallel to the surface in the layers of the mixtures having the molar ratios 95:5, 90:10 and 80:20 (dye/palmitic acid), but were oriented essentially perpendicular to the surface in the layers of the mixtures having a palmitic acid content of 40% or more.

We claim:

1. A film which comprises at least two unimolecular layers of different composition, in each case one layer containing or comprising a compound of the formula I

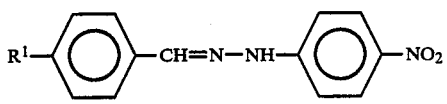

in which $R^1$ denotes the

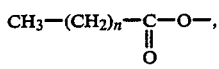

$CH(CH_2)_nN(CH_2)_lH$ or $CH_3(CH_2)_n(CO)N(CH_2)_lH$ radical and m denotes a number from 10 to 25, n denotes a number from 8 to 22 and l denotes a number from 0–25, the molecules thereof being oriented in the same direction, parallel to one another and non-centrosymmetrically, alternating with a layer containing or comprising another amphiphilic compound.

2. A film as claimed in claim 1, which comprises at least two unimolecular layers of different composition, in each case one layer containing or comprising a compound of the formula (I) alternating with a layer containing or comprising an unsaturated amphiphilic compound.

3. A film as claimed in claim 2, wherein the unsaturated amphiphilic compound has the formula III

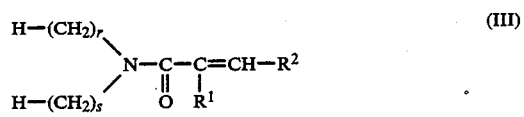

in which $R^1$ denotes H, CL, F, CN or $(CH_2)_tH$, $R^2$ denotes H, $(CH_2)_uH$ or $-CH=CH-(CH_2)_uH$, r and s, independently of one another, denote a number from 0–22 and t and u, independently of one another, denote a number from 0–24.

4. A film consisting essentially of a plurality of oligomolecular layers of an amphiphilic compound wherein each layer contains or comprises a compound of the formula (I)

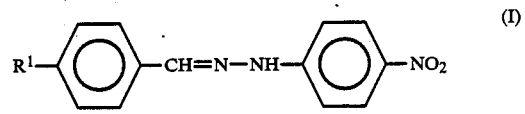

in which $R^1$ denotes the

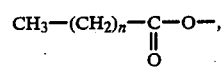

and m denotes a number from 10 to 25, n denotes a number from 8 to 22, and l denotes a number from 0–25, the molecules thereof being oriented in the same direction, parallel to one another and non-centrosymmetrically.

* * * * *

UNITED STATES PATENT AND TRADEMARK OFFICE
CERTIFICATE OF CORRECTION

PATENT NO. : 4,970,120
DATED : 11/13/90
INVENTOR(S) : LASCHEWSKY, ET AL.

It is certified that error appears in the above-identified patent and that said Letters Patent is hereby corrected as shown below:

Column 3, Line 18, "—N    B" should read

-- —N̂B -- .

Column 3, Line 48, after "$CH_3$", please insert

-- ,B -- .

Claim 3, Column 12, Line 29, "CL" should read

-- Cl -- .

Signed and Sealed this

Seventh Day of July, 1992

Attest:

DOUGLAS B. COMER

*Attesting Officer*     Acting Commissioner of Patents and Trademarks